United States Patent [19]
Doshi et al.

[11] Patent Number: 5,948,801
[45] Date of Patent: Sep. 7, 1999

[54] TREATMENT OF RETINAL EDEMA WITH BRINZOLAMIDE

[75] Inventors: Rupa Doshi, Fort Worth; Michael A. Kapin, Arlington, both of Tex.

[73] Assignee: Alcon Laboratories, Inc., Fort Worth, Tex.

[21] Appl. No.: 09/036,960

[22] Filed: Mar. 9, 1998

[51] Int. Cl.$^6$ ..................................................... A61K 31/41
[52] U.S. Cl. ............................................. 514/363; 514/912
[58] Field of Search ...................................... 514/363, 912

[56] References Cited

U.S. PATENT DOCUMENTS 5,240,923  8/1993  Dean et al. .......................... 514/226.5
5,378,703  1/1995  Dean et al. .......................... 514/222.8

FOREIGN PATENT DOCUMENTS

WO 97/30704  8/1997  WIPO .

OTHER PUBLICATIONS

Miller, et al., "Active Transport of Ions Across Frog Retinal Pigment Epithelium," *Experimental Eye Research*, 25:235–248 (1977).

Marmor, et al., "Enhancement of Retinal Adhesion and Subretinal Fluid Resorption by Acetazolamide," Investigative Ophthalmology, 23 (1):121–124 (Jul., 1982).

Marmor, et al., "Pharmacologic Modification of Subretinal Fluid Absorption in the Rabbit Eye," Archives of Ophthalmology, 104:1674–1677 (Nov. 1986).

Cox, et al., "Treatment of Chronic Macular Edema With Acetazolamide," Archives of Ophthalmology, 106:1190–1194 (Sep. 1988).

Borhani, et al., "Vitreoretinal Toxicity of Acetazolamide Following Intravitreal Administration in the Rabbit Eye", Ophthalmic Surgery, 25 (3):166–169 (Mar. 1994).

Grover, et al., "Efficacy of Dorzolamide Hydrochloride in the Management of Chronic Cystoid Macular Edema in Patients with Retinitis Pigmentosa," The Journal of Retinal and Vitreous Diseases, 17(3):222–231 (1997).

*Primary Examiner*—Zohreh Fay
*Attorney, Agent, or Firm*—Sally Yeager

[57] ABSTRACT

Methods for preventing and treating retinal edema with brinzolamide are disclosed.

5 Claims, No Drawings

TREATMENT OF RETINAL EDEMA WITH BRINZOLAMIDE

The present invention is directed to the use of brinzolamide to treat retinal edema.

BACKGROUND OF THE INVENTION

In 1977, Miller, et al., did studies with bullfrogs and found that the pigment epithelium actively secretes sodium and calcium into the retinal space and absorbs chlorine and perhaps bicarbonate and potassium, and that this activity could be important in controlling the ionic milieu in the outer retina. Miller, et al., "Active Transport of Ions Across Frog Retinal Pigment Epithelium," *Experimental Eye Research*, 25:235–248 (1977).

In 1982, Marmor, et al. suggested that acetazolamide (intravenous) might have application in preventing or slowing the spread of retinal detachments or hasten resorption of subretinal fluid. Marmor, et al., "Enhancement of Retinal Adhesion and Subretinal Fluid Resorption by Acetazolamide," *Investigative Ophthalmology*, 23 (1):121–124 (July, 1982). In 1986, it was found that acetazolamide in high doses enhanced subretinal fluid resorption, but had little effect when dosed as ordinarily used. Marmor, et al., "Pharmacologic Modification of Subretinal Fluid Absorption in the Rabbit Eye," *Archives of Ophthalmology*, 104:1674–1677 (Nov. 1986). Clinical studies in 1988 showed that acetazolamide modifies or causes resolution of macular edema in some patients. The studies showed no detectable effect on macular edema due to primary retinal vascular disease in contrast to the macular edema resulting from inflammation or inherited outer retinal disorders. Cox, et al, "Treatment of Chronic Macular Edema With Acetazolamide," *Archives of Ophthalmology*, 106:1190–1194 (September 1988). In 1994, Borhani et al., suggested the intraocular administration (injection) of acetazolamide for treating cystoid macular edema rather that systemic administration due to the serious systemic side effects associated with systemic administration. Borhani, et al., "Vitreoretinal Toxicity of Acetazolamide Following Intravitreal Administration in the Rabbit Eye," *Ophthalmic Surgery*, 25 (3):166–169 (March 1994).

Brinzolamide is disclosed in commonly assigned U.S. Pat. Nos. 5,240,923 and 5,378,703 for its usefulness in controlling intraocular pressure, particularly in the treatment of glaucoma. These patents are incorporated herein by reference.

Retinal edema is treated today with non-steroidal anti-inflammatories, corticosteroids, laser photocoagulation, and systemic acetazolamide. The use of brinzolamide provides an alternative drug for the treatment of this prevalent condition.

SUMMARY OF THE INVENTION

The present invention is directed to the topical use of brinzolamide formulations to treat retinal edema.

DESCRIPTION OF PREFERRED EMBODIMENTS

Retinal edema, including macular edema, also referred to as cystoid macular edema (CME) or cystic macular edema, may develop in association with a variety of ocular conditions. These conditions include, but are not limited to, diabetic retinopathy, ischemic retinopathies (e.g., vein occlusion), posterior segment inflammation, laser photocoagulation, and intraocular surgery, such as cataract removal. The edema is a result of cystic accumulation of extracellular interstitial fluid in the outer plexiform and inner nuclear layers as a result of the breakdown of the blood retinal barrier. The anatomy of the macular region of the retina predisposes it to the development of edema. The macula is a shallow concavity with a central depression, the fovea. The cells in the macular region have a high metabolic activity and the thickness of the outer plexiform layer forms a reservoir for the potential accumulation of extracellular fluid. The central avascular zone creates a watershed arrangement between the choroidal and retinal circulation.

Normally, the accumulation of fluids is prevented by tight junctions joining the endothelium of retinal capillaries creating a "blood-retinal" barrier. In addition, an intact functional retinal pigment epithelium (RPE) also prevents fluids from reaching the inner retina by tight junctions and active transport. Thus, the accumulation of extracellular intraretinal fluid is prevented by osmotic forces, hydrostatic forces, capillary permeability, and tissue compliance, all of which ensure the capillary filtration is equal to the rate of fluid removal. Typically, edema occurs as a result of one or more of the following: (a) injury to the cellular components due to hypoxia or ischemia (cytotoxic edema), (b) primary breakdown in the blood brain barrier (vasogenic edema), and (c) decreased fluid resorption due to RPE dysfunction.

Brinzolamide, (R-(+)-4-ethylamino-3,4-dihydro-2-(3-methoxy)propyl-2H-thieno [3,2,e]1,2-thiazine-6-sulfonamide-1,1-dioxide, is a carbonic anhydrase inhibitor which has been found to be effective in lowering the elevated intraocular pressure associated with intraocular hypertension and glaucoma, but surprisingly, we have found that brinzolamide is well-suited to penetrate into the retina, choroid, and optic nerve head upon topical ocular administration and is effective in preventing and/or reducing retinal edema.

Brinzolamide can be administered topically to the eye, systemically (250–1000 mg/day), or via intravitreal (0.1–10 mg/eye), or periocular (0.1–50 mg/eye) injections. In order to prevent the edema associated with laser photocoagulation, it is preferrable to administer brinzolamide prior to and/or following the laser procedure.

Brinzolamide is preferably formulated as a topical ophthalmic suspension with a pH of about 4.5–7.8. It will normally be contained in the formulation at a concentration of 0.005–10% by weight, preferably 0.25% to 5.0% by weight. Thus, for topical presentation, one to three drops of these formulations will be delivered to the surface of the eye one to four times a day according to the routine discretion of a skilled clinician.

The following example is the preferred formulation for use according to the present invention:

EXAMPLE

| Ingredient | Percent w/v |
| --- | --- |
| Brinzolamide | 1.0 |
| Mannitol | 3.3 |
| Carbopol 974P | 0.4 |
| Tyloxapol | 0.025 |
| Disodium EDTA | 0.01 |
| Benzalkonium Chloride | 0.01 + 5% excess |
| Sodium Chloride | 0.25 |
| Sodium Hydroxide/Hydrochloric Acid | pH 7.5 |

| Ingredient | Percent w/v |
| --- | --- |
| Purified Water | QS 100 |

We claim:

1. A method for treating retinal edema which comprises administering a pharmaceutically effective amount of brinzolamide.

2. The method of claim 1 wherein the brinzolamide is administered systemically, topically to the eye, or via intraocular or periocular injection.

3. The method of claim 2 wherein the brinzolamide is administered topically to the eye.

4. The method of claim 3 wherein the brinzolamide is administered at a concentration of 0.005–10 percent by weight.

5. The method of claim 4 wherein the brinzolamide concentration is 0.25–5.0 percent by weight.

* * * * *